(12) United States Patent
Nel et al.

(10) Patent No.: US 9,061,952 B2
(45) Date of Patent: Jun. 23, 2015

(54) FISCHER-TROPSCH SYNTHESIS

(71) Applicant: SASOL TECHNOLOGY (PROPRIETARY) LIMITED, Johannesburg (ZA)

(72) Inventors: Hermanus Gerhardus Nel, Parys (ZA); Alex Philip Vogel, Vereeniging (ZA)

(73) Assignee: Sasol Technology (Propietary) Limited, Johannesburg (ZA)

( * ) Notice: Subject to any disclaimer, the term of this patent is extended or adjusted under 35 U.S.C. 154(b) by 0 days.

(21) Appl. No.: 14/379,482

(22) PCT Filed: Feb. 20, 2013

(86) PCT No.: PCT/IB2013/051364
§ 371 (c)(1),
(2) Date: Aug. 18, 2014

(87) PCT Pub. No.: WO2013/124793
PCT Pub. Date: Aug. 29, 2013

(65) Prior Publication Data
US 2015/0018437 A1    Jan. 15, 2015

Related U.S. Application Data

(60) Provisional application No. 61/602,820, filed on Feb. 24, 2012.

(30) Foreign Application Priority Data

Feb. 24, 2012   (ZA) .................................. 201201405

(51) Int. Cl.
C07C 27/06    (2006.01)
C07C 1/04    (2006.01)
C10G 2/00    (2006.01)

(52) U.S. Cl.
CPC ................ *C07C 1/0485* (2013.01); *C10G 2/32* (2013.01); *C10G 2/332* (2013.01); *C07C 1/0435* (2013.01); *C07C 2523/75* (2013.01)

(58) Field of Classification Search
CPC .......................... C07C 1/0485; C07C 2523/75
USPC ................................................... 518/705, 715
See application file for complete search history.

(56) References Cited

U.S. PATENT DOCUMENTS 7,776,932 B2    8/2010    Marion et al.

FOREIGN PATENT DOCUMENTS

| EP | 1746143 A1 | 1/2007 |
|---|---|---|
| GB | 2444055 A | 5/2008 |
| WO | WO 03/068715 A1 | 8/2003 |
| WO | WO 2007/065904 A1 | 6/2007 |

OTHER PUBLICATIONS

European Patent Office, *International Search Report*, dated Jun. 19, 2013, issued in International Application No. PCT/IB2013/051364.
European Patent Office, *International Preliminary Report on Patentability (Chapter II of the Patent Cooperation Treaty)*, dated Apr. 14, 2014, issued in International Application No. PCT/IB2013/051364.

*Primary Examiner* — Sudhakar Katakam
(74) *Attorney, Agent, or Firm* — Klarquist Sparkman, LLP

(57) ABSTRACT

A process (10) to produce Fischer-Tropsch products includes feeding feed synthesis gas (30) with a substantially constant target feed synthesis gas $H_2/CO$ ratio to a Fischer-Tropsch synthesis stage (16). A portion of the feed synthesis gas (30) is converted to Fischer-Tropsch products in the Fischer-Tropsch synthesis stage (16). The Fischer-Tropsch products (20) from the Fischer-Tropsch synthesis stage (16) are withdrawn. A Fischer-Tropsch synthesis stage tail gas (26) which includes unconverted $H_2$ and CO is obtained. The operating conditions of the Fischer-Tropsch synthesis stage (16) are manipulated to achieve a substantially constant target tail gas $H_2/CO$ ratio, with the target tail gas $H_2/CO$ ratio being substantially different from the target feed synthesis gas $H_2/CO$ ratio.

8 Claims, 6 Drawing Sheets

FISCHER-TROPSCH SYNTHESIS

CROSS REFERENCE TO RELATED APPLICATIONS

Figure 1:
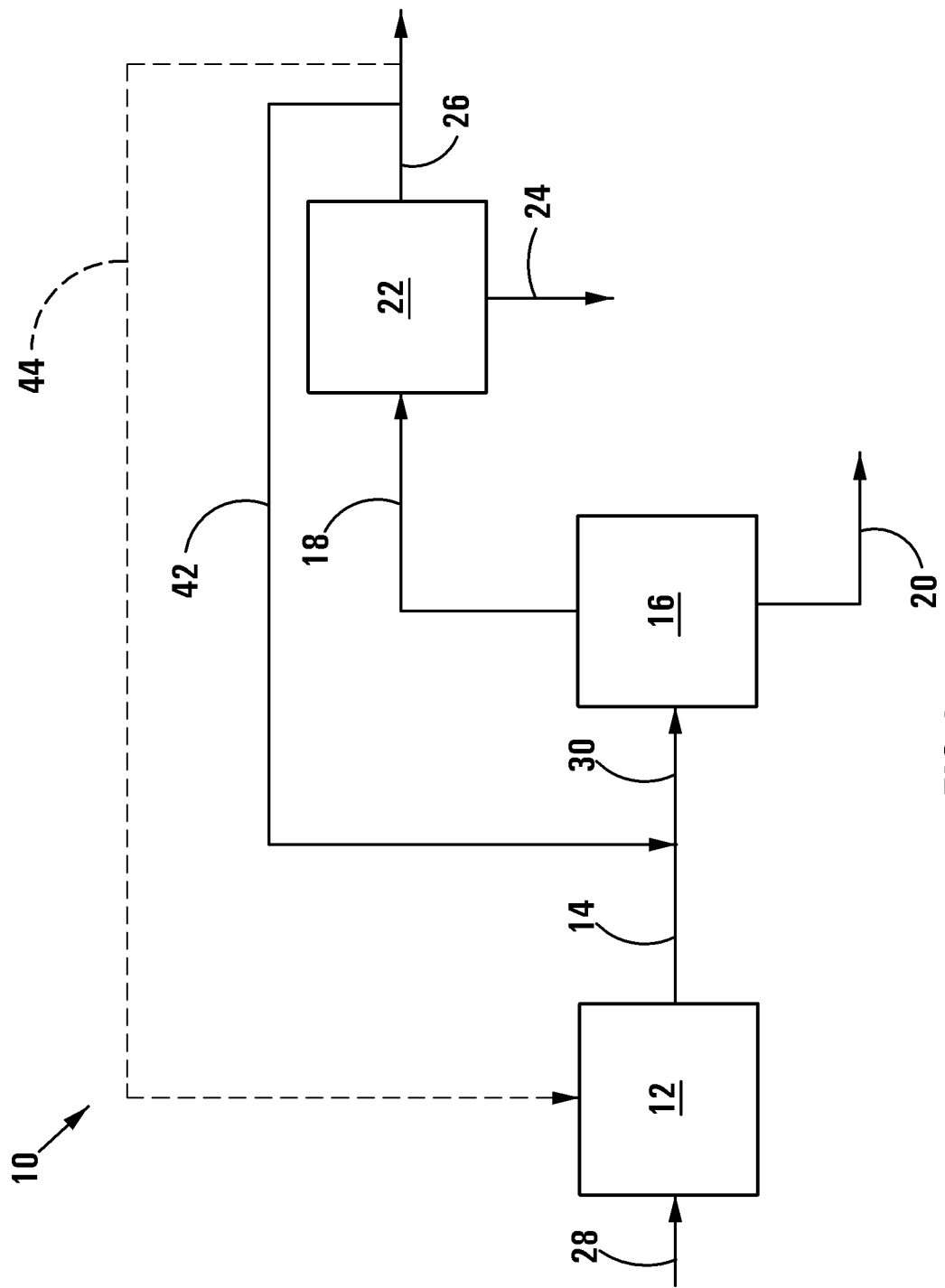

This is the U.S. National Stage of International Application No. PCT/IB2013/051364, filed Feb. 20, 2013, which claims the benefit of U.S. Provisional Application No. 61/602,820, filed Feb. 24, 2012, and which claims the benefit of South Africa Application No. 2012/01405, filed Feb. 24, 2012.

FIELD OF THE INVENTION

This invention relates to Fischer-Tropsch synthesis. In particular, the invention relates to a process to produce Fischer-Tropsch products.

BACKGROUND OF THE INVENTION

In Fischer-Tropsch synthesis, synthesis gas (a mixture of CO and $H_2$) is converted to a range of hydrocarbons (from normally gaseous to waxy material) and water. If a so-called shifting catalyst is employed, some of the product water reacts with CO according to the water gas shift reaction to form $CO_2$ and $H_2$. Iron-based catalysts typically have a high activity for the water gas shift reaction and are therefore regarded as shifting catalysts. However, some catalysts, for example those based on cobalt or ruthenium, do not have a high activity for the water gas shift reaction and therefore produce very small amounts of $CO_2$ via the water gas shift reaction. These catalysts, known as non-shifting catalysts, typically have a $CO_2$ selectivity of less than about 2%, i.e. less than about 2% of the total CO consumed in the synthesis process is converted to $CO_2$.

The Fischer-Tropsch reaction per se consumes $H_2$ and CO in a ratio of about 2, i.e. has a $H_2$/CO consumption ratio or usage ratio of about 2. Depending on the selectivity towards light hydrocarbons, especially methane, this consumption ratio is pushed up to slightly above 2, e.g. 2.05. On the other hand, the conversion of some CO to $CO_2$ via the water gas shift reaction tends to lower the usage ratio by consuming CO and producing $H_2$. Therefore, the overall usage ratio of the synthesis gas is typically in the range of 2-2.1 for a non-shifting Fischer-Tropsch process, while it can be substantially below 2 for a shifting Fischer-Tropsch process. A drift over time in the product spectrum produced with a Fischer-Tropsch catalyst, e.g. an increase over time of the selectivity towards methane and lighter hydrocarbon products, can slightly affect the usage ratio. Furthermore, a change in the relative rates of the Fischer-Tropsch and water gas shift reactions over the catalyst can substantially change the usage ratio. Nevertheless, in commercial operations steps are normally taken to limit such variations, such as periodic regeneration or rejuvenation of the catalyst or online catalyst replacement yielding normally a substantially constant usage ratio for a commercial Fischer-Tropsch process.

It is well known that the selectivity behaviour of Fischer-Tropsch catalysts is strongly influenced by the $H_2$/CO ratio, with lower ratios favouring the production of desired heavy products. For this reason, Fischer-Tropsch synthesis processes are sometimes operated at $H_2$/CO ratios that are lower than the $H_2$/CO usage ratio. It follows by simple mass balance, that the $H_2$/CO ratio in the reactor outlet will then be different from the feed $H_2$/CO ratio. It will be appreciated that when recycle around a Fischer-Tropsch reactor is then employed, the $H_2$/CO ratio of the feed to the reactor becomes a difficult to control parameter as a result of positive feedback in the system. It would therefore be an advantage if a method could be found that facilitates operation with a stable $H_2$/CO ratio.

For commercial applications, a Fischer-Tropsch reactor and its synthesis loop normally form part of a larger plant which, amongst others, includes a synthesis gas generation stage, such as gas reforming or coal gasification. The tail gas from the Fischer-Tropsch synthesis stage is often employed elsewhere in the larger plant. For example, some or all of the tail gas can be recycled to the synthesis gas generation stage in order to assist in producing a synthesis gas of the required composition ($H_2$/CO ratio) by providing a $CO_2$-rich feedstream. All or some of the tail gas can also be used for further chemical conversion downstream of the Fischer-Tropsch reactor. Due to the highly integrated nature of such petrochemical plants, and the fact that gaseous streams (with consequently limited capacity for buffering) are flowing between plant units or stages, stable operation of such integrated complexes present challenges. A method is therefore also required efficiently to achieve or facilitate this.

U.S. Pat. No. 7,776,932 discloses the control of an integrated Fischer-Tropsch process by determining the $H_2$/CO ratio in both the feed to the Fischer-Tropsch synthesis stage (A1), as well as in the effluent from the Fischer-Tropsch synthesis stage (A2), and adjusting the $H_2$ and/or CO in the synthesis gas feed to the Fischer-Tropsch synthesis stage to keep the difference between A1 and A2 essentially constant. This is achieved by controlling the operation of the synthesis gas generation stage, which adjusts the $H_2$/CO ratio in the feed to the Fischer-Tropsch synthesis. In this process the ratios A1 and A2 are therefore allowed to vary, with the difference between A1 and A2 being maintained constant.

WO 2002/038699 teaches a method of controlling the feed $H_2$/CO ratio to the Fischer-Tropsch synthesis reactor by recycling an $H_2$ or $CO_2$ containing stream to a reformer and feeding the reformed gas to the Fischer-Tropsch synthesis reactor.

US 2004/014825 discloses a system where two synthesis gas streams, one with an $H_2$/CO ratio above 2 and one with an $H_2$/CO ratio below 2, together form the feed to a Fischer-Tropsch reactor. The composition of the tail gas stream from the Fischer-Tropsch reactor is measured and the flow rate of one of the two feed streams is adjusted depending upon the composition of the tail gas stream. In one embodiment of the invention, the ratio of partial pressures of $H_2$ and CO in the tail gas is used to adjust the flow rate of the two reactor feed streams. In other words, US 2004/014825 also teaches the control of the outlet $H_2$/CO ratio by adjusting the overall inlet $H_2$/CO ratio.

U.S. Pat. No. 5,023,276 teaches a method of controlling the $H_2$/CO ratio of synthesis gas produced in an autothermal reformer, the method including the removal of $CO_2$ from the reformer effluent, and recycling some or all of the $CO_2$ back to the reformer inlet. Additionally, the effluent from a Fischer-Tropsch synthesis reactor can also be recycled to the reformer inlet. By controlling the proportions of the various feed streams to the reformer, the desired $H_2$/CO ratio is obtained for the Fischer-Tropsch synthesis.

The above references therefore teach various methods of obtaining a synthesis gas with the desired $H_2$/CO ratio from a synthesis gas generation stage in order to ensure an appropriate feed composition to a Fischer-Tropsch synthesis stage. These references further teach methods of control of a Fischer-Tropsch synthesis process which involve varying the inlet $H_2$/CO ratio to the Fischer-Tropsch reactor in order to obtain a desired outlet $H_2$/CO ratio.

Water formed in the Fischer-Tropsch synthesis process can have a detrimental effect on the catalyst and is one of the leading causes of catalyst deactivation. Usually there is a limiting value of water partial pressure above which serious catalyst deactivation occurs. This point normally represents an operating constraint for the process. This constraint can assume a variety of mathematical forms, and can be as simple as the absolute water partial pressure or the ratio of the water partial pressure to that of one or both of the reagents CO and $H_2$. More complex functional relationships between water partial pressure and one or both of the reagents CO and $H_2$, or a combination of constraints, can also be applied to ensure a safe operating window for the Fischer-Tropsch catalyst in terms of the water partial pressure.

It is not readily possible directly to measure the partial pressures of water and reagents inside or at the outlet of a commercial Fischer-Tropsch reactor. A broad range of components is typically contained in the Fischer-Tropsch reactor outlet, and includes unconverted CO and $H_2$, as well as $CO_2$, $H_2O$ and light hydrocarbons. This severely complicates quantitative analysis of such samples, as some components (water and hydrocarbons) are condensable at ambient conditions. It is also not easy to identify a detector that can quantitatively analyse such a variety of components. Clearly a method is required which allows for an accurate and fast determination of these partial pressures inside the Fischer-Tropsch reactor, as well as a quick response to make corrective actions as required.

Once certain operating parameters of the Fischer-Tropsch synthesis (e.g. total pressure, water content in the feed (i.e. conditions of water knock-out)) are essentially fixed at constant values, it is then possible to fairly relate the water partial pressure to the extent of conversion achieved inside the reactor (the so-called per pass conversion or single pass conversion). In addition, provided the Fischer-Tropsch synthesis has a reasonably constant usage ratio and feed gas $H_2$/CO ratio, it is also possible to fairly relate a mathematical relationship between the partial pressures of water and the reactants to the per pass conversion. In other words, ensuring a safe operating window for the Fischer-Tropsch catalyst in terms of the water partial pressure is essentially reduced to controlling the per pass conversion. This critical per pass conversion can be determined by those skilled in the art from specified process conditions and constraints.

However, determining the per pass conversion achieved on an operating commercial Fischer-Tropsch process is not a straightforward matter as will be illustrated below. It will be appreciated by those skilled in the art that the conversion achieved in a Fischer-Tropsch reactor can be expressed in a variety of ways, e.g. in terms of the CO conversion, the $H_2$ conversion or the (CO+$H_2$) conversion. For purposes of illustration, the following explanation will be based on the CO conversion.

The per pass CO conversion of a Fischer-Tropsch synthesis process can be expressed as follows:

$$\chi_{CO} = \frac{F_{In}C_{In}^{CO} - F_{Out}C_{Out}^{CO}}{F_{In}C_{In}^{CO}}$$

where $F_{In}$ and $F_{Out}$ are the total inlet and outlet volumetric flow rates of gas (at normal conditions) of the Fischer-Tropsch reactor, respectively, and $C_{In}^{CO}$ and $C_{Out}^{CO}$ are the volumetric concentrations of CO in the inlet and outlet gas streams, respectively. Each of these four parameters needs to be measured independently and accurately in order to calculate the conversion, whereafter corrective action needs to be taken to ensure maximum conversion while not exceeding the upper conversion limit constraint. However, this is not trivial to achieve, especially not for large scale commercial plants where gas flow rates are very high. For example, flow meters need to be calibrated and also require some physical data from the gas stream (e.g. density), which can change with process variations. The CO concentration in the gas stream will usually be obtained by analysing one or more samples of the streams, e.g. on a gas chromatograph. A broad range of components is typically contained in such streams, especially in the Fischer-Tropsch reactor outlet, and includes unconverted CO and $H_2$, as well as $CO_2$, $H_2O$ and light hydrocarbons. This severely complicates quantitative analysis of such samples, as some components (water and hydrocarbons) are condensable at ambient conditions. It is also not easy to identify a detector that can quantitatively analyse such a variety of components. A further source of uncertainty in the calculated conversion is the principle of error propagation, which dictates that the errors contained in the individually measured quantities are amplified via the mathematical calculations performed. It is therefore clear that this approach of estimating the conversion achieved on a large scale reactor will be subject to significant error and uncertainty. A substantially larger safety margin then needs to be built in to avoid accidentally exceeding the operating limits, which implies that the process will generally not be operated close to the optimum operating point. It will therefore be an advantage if a method can be found that enables fairly estimating the per pass conversion.

It will be appreciated by those skilled in the art that the same problems are encountered when the object is to calculate and control the overall conversion achieved in a Fischer-Tropsch reactor, e.g. the overall conversion when recycle around the reactor is also taken into account.

In the design phase of a Fischer-Tropsch synthesis process, a broad range of conditions (e.g. pressures, $H_2$/CO feed ratios, etc.) are normally explored in order to locate the optimum operating point for the design. During the design phase, the constraints with respect to water are applied in order to ensure that the catalyst operating limits are not exceeded, i.e. to ensure a safe operating window for the Fischer-Tropsch catalyst in terms of the water partial pressure. This typically also considers per pass conversion and overall conversion among other considerations. Commercial plants are however designed and operate to ensure operation at optimum performance. This optimum operating point or region will generally be close to the constraints related to the water partial pressure to maximise productivity and process efficiency. The challenge is therefore to operate a commercial plant as close to these limits as possible to achieve maximum process efficiency, while not exceeding applicable limits in order to protect the integrity of the catalyst. It will be appreciated that such a control philosophy is not trivial, amongst others due to the large scale at which such Fischer-Tropsch processes are operated. For example, the production capacity of a single Fischer-Tropsch slurry bubble column reactor is being pushed beyond 20 000 bbl/day. This means that the transient behaviour of the system, compounded by the enormous heat generation and complicated chemistry, is complex and difficult to predict. Large deviations from set points can result in runaway situations with serious detrimental effects.

BRIEF DESCRIPTION OF THE INVENTION

According to the invention there is provided a process to produce Fischer-Tropsch products, the process including feeding feed synthesis gas with a substantially constant target feed synthesis gas $H_2/CO$ ratio to a Fischer-Tropsch synthesis stage;

converting a portion of said feed synthesis gas to Fischer-Tropsch products in the Fischer-Tropsch synthesis stage;

withdrawing said Fischer-Tropsch products from the Fischer-Tropsch synthesis stage;

obtaining a Fischer-Tropsch synthesis stage tail gas which includes unconverted $H_2$ and CO; and manipulating operating conditions of the Fischer-Tropsch synthesis stage to achieve a substantially constant target tail gas $H_2/CO$ ratio, said target tail gas $H_2/CO$ ratio being substantially different from the target feed synthesis gas $H_2/CO$ ratio.

In this specification, the term "tail gas $H_2/CO$ ratio" should be understood to mean the $H_2/CO$ ratio of any gaseous stream that has been derived from gaseous material withdrawn from the Fischer-Tropsch synthesis stage without significantly affecting the $H_2/CO$ ratio of that gaseous stream. This may include, but is not limited to, the direct gaseous material withdrawn from a Fischer-Tropsch reactor before or after cooling and Fischer-Tropsch product knock-out, an internal gaseous recycle stream, a gaseous stream leaving the Fischer-Tropsch synthesis stage, and the like. Thus, to be clear, the tail gas may be a gaseous product stream from a Fischer-Tropsch reactor, or a gaseous stream obtained from the gaseous product stream from a Fischer-Tropsch reactor. The term "Fischer-Tropsch synthesis stage" should be understood to include either one Fischer-Tropsch reactor, or multiple Fischer-Tropsch reactors connected in series or in parallel, or multiple Fischer-Tropsch reactors connected with some in series and some in parallel.

In this specification, the term "substantially constant target feed synthesis gas $H_2/CO$ ratio" or "substantially constant target tail gas $H_2/CO$ ratio" should be understood to mean a $H_2/CO$ ratio that is within about 10% of the target $H_2/CO$ ratio, preferably within about 8% of the target $H_2/CO$ ratio, more preferably, within about 5% of the target $H_2/CO$ ratio, most preferably within about 3% of the target $H_2/CO$ ratio of the stream concerned.

In this specification, by "substantially different" is meant that the target tail gas $H_2/CO$ ratio differs from the target feed synthesis gas $H_2/CO$ ratio by at least about 10%, but may even be higher at at least about 20%, or even higher at at least about 50%, e.g. about 30%.

The process of the present invention is therefore operated with a substantially constant target feed synthesis gas $H_2/CO$ ratio entering the Fischer-Tropsch synthesis stage, and in particular entering said one or more Fischer-Tropsch reactors. In addition, the target tail gas $H_2/CO$ ratio (i.e. target gaseous product $H_2/CO$ ratio) is substantially different from the target feed synthesis gas $H_2/CO$ ratio. It follows from mass balance that the feed synthesis gas $H_2/CO$ ratio is therefore necessarily substantially different from the $H_2/CO$ usage ratio. Under such circumstances, and as will be set out in more detail hereinafter, there is a one to one mapping between the tail gas $H_2/CO$ ratio and the per pass conversion of reactants in the Fischer-Tropsch synthesis stage, assuming a reasonably constant $H_2$ and CO usage ratio. By manipulating operating conditions of the Fischer-Tropsch synthesis stage to achieve a constant target tail gas $H_2/CO$ ratio, one therefore achieves a constant target per pass conversion.

The Fischer-Tropsch synthesis stage may be a non-shifting or a shifting Fischer-Tropsch synthesis stage. Preferably the Fischer-Tropsch synthesis stage is a non-shifting Fischer-Tropsch synthesis stage employing a cobalt-based catalyst.

In order to achieve the target tail gas $H_2/CO$ ratio, the operating conditions of the Fischer-Tropsch synthesis stage may be manipulated by a variety of methods known in the art. Thus, manipulating operating conditions of the Fischer-Tropsch synthesis stage to achieve a constant target tail gas $H_2/CO$ ratio may include adjusting a feed synthesis gas flow rate to the Fischer-Tropsch synthesis stage, adjusting an operating temperature of the Fischer-Tropsch synthesis stage, changing the amount and/or average activity of a catalyst in the Fischer-Tropsch synthesis stage by loading or unloading of catalyst, or any combination of such methods. For example, the methods disclosed in WO 2012/056346 may be employed to achieve the target tail gas $H_2/CO$ ratio.

The feed synthesis gas may be a combination of fresh synthesis gas and recycled Fischer-Tropsch synthesis stage tail gas which includes unconverted $H_2$ and CO, whether combined into a single stream or fed separately to the Fischer-Tropsch reaction stage. Thus, the process may include recycling a portion of the Fischer-Tropsch synthesis stage tail gas which includes unconverted $H_2$ and CO to the Fischer-Tropsch synthesis stage.

In one embodiment of the invention, the ratio of the recycled Fischer-Tropsch synthesis stage tail gas to the fresh synthesis gas is manipulated to achieve said feed synthesis gas with a substantially constant target feed synthesis gas $H_2/CO$ ratio.

Typically, in this embodiment, the fresh synthesis gas and the recycled Fischer-Tropsch synthesis stage tail gas which includes unconverted $H_2$ and CO are physically combined before being fed into the Fischer-Tropsch synthesis stage as the feed synthesis gas with a substantially constant target feed synthesis gas $H_2/CO$ ratio.

The process may include operating a synthesis gas generation stage to produce said fresh synthesis gas.

In another embodiment of the invention, the synthesis gas generation stage is operated to produce fresh synthesis gas with a substantially constant target fresh synthesis gas $H_2/CO$ ratio. Preferably, in this embodiment of the invention, the fresh synthesis gas is maintained at a constant flow rate and the operating conditions or parameters (e.g. temperature, catalyst loading, average catalyst age, etc.) of the Fischer-Tropsch synthesis stage are adjusted in order to achieve the target tail gas $H_2/CO$ ratio. As will be appreciated, in this embodiment of the invention, an expensive to operate synthesis gas generation stage can advantageously be operated at constant and full capacity.

In embodiments where the synthesis gas generation stage is operated to produce fresh synthesis gas with a substantially constant target fresh synthesis gas $H_2/CO$ ratio and the feed synthesis gas is a combination of the fresh synthesis gas and recycled Fischer-Tropsch synthesis stage tail gas, the recycled Fischer-Tropsch synthesis stage tail gas is then preferably fed to the Fischer-Tropsch synthesis stage in a fixed ratio to the fresh synthesis gas, thereby achieving said substantially constant target feed synthesis gas $H_2/CO$ ratio. It will be appreciated that this approach, together with feeding the fresh synthesis gas with a substantially constant target fresh synthesis gas $H_2/CO$ ratio to the Fischer-Tropsch synthesis stage and manipulating the operating conditions of the Fischer-Tropsch synthesis stage to achieve a constant target tail gas $H_2/CO$ ratio, effectively fixes the total feed $H_2/CO$ ratio. The per pass Fischer-Tropsch synthesis stage conversion is then also uniquely related to the tail gas $H_2/CO$ ratio.

Operating a synthesis gas generation stage to produce a fresh synthesis gas with a substantially constant target fresh synthesis gas $H_2/CO$ ratio may include recycling at least a portion of the Fischer-Tropsch synthesis stage tail gas, or a CO and/or $H_2$ containing gas stream derived from the Fischer-Tropsch synthesis stage tail gas, to the synthesis gas generation stage.

The rate at which the Fischer-Tropsch synthesis stage tail gas or said gas stream derived from the Fischer-Tropsch synthesis stage tail gas is recycled to the synthesis gas generation stage may be manipulated to produce said fresh synthesis gas with a substantially constant target fresh synthesis gas $H_2/CO$ ratio.

The process may include cooling the tail gas withdrawn from the Fischer-Tropsch synthesis stage to condense water and optionally other condensable components of the tail gas, including Fischer-Tropsch products, and to provide a cooled tail gas stream.

At least a portion of the cooled tail gas stream may be employed as the recycled Fischer-Tropsch synthesis stage tail gas.

DETAILED DESCRIPTION OF PREFERRED EMBODIMENTS OF THE INVENTION

The invention will be further described, by way of example, with reference to the following diagrammatic drawings.

In the drawings:

FIG. 1 is a diagrammatic representation of a process in accordance with the invention to produce Fisher-Tropsch products; and FIGS. 2-6 show graphs of Fischer-Tropsch tail gas $H_2/CO$ molar ratio as a function of CO conversion, for various $H_2$ and CO consumption ratios.

With reference to FIG. 1, reference numeral 10 generally indicates one embodiment of a process in accordance with the invention to produce Fisher-Tropsch products. The process 10 includes broadly a synthesis gas generation stage 12, a Fischer-Tropsch synthesis stage 16 and a cooling stage 22.

Carbonaceous or hydrocarbonaceous feed material 28 is fed to the synthesis gas generation stage 12 which is operated to produce fresh synthesis gas 14 which includes $H_2$ and CO. The fresh synthesis gas 14 is fed to the Fischer-Tropsch synthesis stage 16 in which the $H_2$ and CO are catalytically converted into Fischer Tropsch liquid products and gaseous products. The gaseous products include unreacted $H_2$ and CO.

The synthesis gas generation stage 12 may be any synthesis gas generation stage, e.g. a coal gasification stage or a natural gas reforming stage, producing a synthesis gas which is suitable for Fischer-Tropsch synthesis. The synthesis gas generation stage 12 may employ combinations of more than one synthesis gas generation technology that may be supplied with different feedstocks, e.g. a combination of coal gasification and reforming of Fischer-Tropsch tail gas, or combinations of different natural gas reforming technologies such as partial oxidation reforming, autothermal reforming and steam reforming. The synthesis gas from the synthesis gas generation stage 12 may be subjected to one or more gas cleaning steps (not shown), where known Fischer-Tropsch catalyst poisons (e.g. $H_2S$, COS, $NH_3$, etc.) or other components (e.g. $CO_2$) are removed from the synthesis gas prior to the Fischer-Tropsch synthesis stage 16. The operation of such a synthesis gas generation stage 12 and optional gas clean-up steps are well known to those skilled in the art and is thus not described in any detail. Similarly, the operation of a Fischer-Tropsch synthesis stage is well known to those skilled in the art and the Fischer-Tropsch synthesis stage 16 is thus not described in any detail.

The Fischer-Tropsch liquid products are withdrawn as a liquid product stream 20 from the Fischer-Tropsch synthesis stage 16. Also, the gaseous products containing unreacted $H_2$ and CO are withdrawn from the Fisher-Tropsch synthesis stage 16 as a gaseous product stream 18. The gaseous product stream 18 from the Fisher-Tropsch synthesis stage 16 is cooled in the cooling stage 22 to condense water and other condensable components therefrom, with the condensed components being separated and withdrawn as a stream 24. Cooled tail gas 26 containing unreacted $H_2$ and CO is withdrawn from the cooling stage 22.

The process 10 can be operated in one of at least two different modes in accordance with the invention. In the first mode of operation, the synthesis gas generation stage 12 and the Fischer-Tropsch synthesis stage 16 are both operated such that substantially constant selected or target $H_2/CO$ ratios in the fresh synthesis gas 14 and in the gaseous product stream 18 are produced. The substantially constant selected or target $H_2/CO$ ratios in the fresh synthesis gas 14 and in the gaseous product stream 18 are not the same.

The operating conditions of the synthesis gas generation stage 12 are manipulated or controlled to achieve the substantially constant selected or target $H_2/CO$ ratio in the fresh synthesis gas 14. In the first mode of operation of the process 10, this includes recycling at least a portion of the cooled tail gas 26 derived from the gaseous product stream 18, as recycled tail gas in flow line 44 (shown in broken lines in FIG. 1), to the synthesis gas generation stage 12. Other methods known to those skilled in the art to adjust the ratio of $H_2/CO$ in the fresh synthesis gas 14 may naturally instead, or in addition, be employed.

In order to achieve the target tail gas $H_2/CO$ ratio, the operating conditions of the Fischer-Tropsch synthesis stage 16 stage can be manipulated by a variety of methods known to those skilled in the art. For example, the flow rate of the fresh synthesis gas 14 being fed to the Fischer-Tropsch synthesis stage 16 may be manipulated or controlled, or an operating temperature of the Fischer-Tropsch synthesis stage 16 may be adjusted, or the amount and/or average activity of a catalyst (preferably a non-shifting cobalt based catalyst) employed in the Fischer-Tropsch synthesis stage 16 may be changed by loading or unloading of catalyst. Any combination of these methods, which affect the conversion of $H_2$ and CO in the Fischer-Tropsch synthesis stage 16, and thus also the water partial pressure, may also be employed.

In the first mode of operation of the process 10, at least a portion of the gaseous products produced by the Fischer-Tropsch synthesis stage 16 is also recycled back to the Fischer-Tropsch synthesis stage 16, as recycle tail gas as indicated by flow line 42. As will be appreciated, the recycle tail gas in flow line 42 also has the same target tail gas $H_2/CO$ ratio as the cooled tail gas 26 and the gaseous product stream 18. Importantly however, the recycle tail gas is recycled such that a substantially constant target feed synthesis gas $H_2/CO$ ratio for the Fischer-Tropsch synthesis stage 16 is maintained. This can be achieved by maintaining a fixed ratio between the flow rate of the fresh synthesis gas feed 14 to the Fischer-Tropsch synthesis stage 16 and the flow rate of the recycle tail gas in flow line 42. As a result, a feed synthesis gas 30 entering the Fischer-Tropsch synthesis stage 26 thus has a substantially constant target feed synthesis gas $H_2/CO$ ratio.

In the second mode of operation of the process 10, the synthesis gas generation stage 12 is operated to produce fresh synthesis gas 14 containing $H_2$ and CO. The $H_2$ and CO molar ratio of the fresh synthesis gas 14 is however not necessarily controlled to be substantially constant as is the case of the first mode of operation of the process 10. The fresh synthesis gas 14, containing $H_2$ and CO, is fed to the Fischer-Tropsch synthesis stage 16 and catalytically reacted as hereinbefore described to produce Fischer Tropsch liquid products withdrawn as the liquid product stream 20, with gaseous products being withdrawn from the Fischer-Tropsch synthesis stage 16 as the gaseous product stream 18.

As hereinbefore described, the gaseous product stream 18 from the Fisher-Tropsch synthesis stage 16 is cooled in the cooling stage 22 to condense water and other condensable components therefrom, with the condensed components being separated and withdrawn as the stream 24. Cooled tail gas 26 is withdrawn from the cooling stage 22. In the second mode of operation of the process 10, at least a portion of the cooled tail gas 26 is recycled to the Fischer-Tropsch synthesis stage 16 in the flow line 42. There is no recycle of cooled tail gas 26 via flow line 44 to the synthesis gas generation stage 12 as in the case of the first mode of operation of the process 10, or if there is such recycle, it does not necessarily serve to produce a substantially constant $H_2$ and CO molar ratio in the fresh synthesis gas 14.

The fresh synthesis gas 14 is combined with cooled recycle tail gas in the flow line 42 to form the feed synthesis gas 30, before being fed to the Fischer-Tropsch synthesis stage 16.

In the second mode of operation of the process 10, the Fischer-Tropsch synthesis stage 16 is controlled or operated such that a substantially constant selected or target $H_2$/CO molar ratio in the gaseous product stream 18, and hence in the cooled tail gas 26 and in the cooled recycle tail gas in the flow line 42, is produced. Furthermore, the flow rate of cooled recycle tail gas in flow line 42 is also controlled to ensure that a substantially constant selected or target $H_2$/CO ratio in the feed synthesis gas 30 is achieved. In the second mode of operation, although the fresh synthesis gas 14 does not necessarily have a substantially constant selected or target $H_2$/CO ratio, this is corrected by controlling the addition of the recycle tail gas from the flow line 42 to the fresh synthesis gas 14 thereby to ensure a substantially constant selected or target $H_2$/CO ratio in the feed synthesis gas 30.

An advantage of the process 10 as illustrated is that the process 10 merely requires the determination of the $H_2$/CO ratio in the fresh synthesis gas 14 (in the first mode of operation) or in the feed synthesis gas 30 and in the gaseous product stream 18 or cooled tail gas 26 of the Fischer-Tropsch synthesis stage 16, to ensure that reactor conversion can be maintained at a desired level to keep water concentrations at acceptable levels. This can typically be done quickly and accurately, since a comprehensive analysis of these streams is not necessary. The analysis technique or apparatus being used, e.g. a mass spectrometer or a gas chromatograph equipped with a thermoconductivity detector (TCD), merely needs to determine the relative amounts of $H_2$ and CO in the streams 14 or 30 on the one hand, and in the streams 18 or 26 on the other hand. This means that the broad spectrum of components in the any of these streams, with a variety of properties, some components being condensable at ambient conditions, does not complicate the analysis. The need for measuring gas flow rates of these streams for purposes of controlling the Fischer-Tropsch reaction stage 16 is also avoided. Further advantages include that the process 10 can in principle always be operated at the optimum design point and that operation in this manner facilitates stable operation of a Fischer-Tropsch synthesis gas loop, including the synthesis gas generation stage 12, and of other possible downstream users of the cooled Fischer-Tropsch tail gas 26.

A non-shifting Fischer-Tropsch process such as the Fisher-Tropsch process 10, consumes $H_2$ and CO in a molar ratio of about 2. Depending on the selectivity towards light hydrocarbons, especially methane, this consumption ratio is pushed up to slightly above 2, e.g. 2.05. If the molar ratio of $H_2$/CO in the fresh synthesis gas 14 or feed synthesis gas 30 to the Fischer-Tropsch synthesis stage 16 is the same as the consumption molar ratio, the $H_2$/CO molar ratio of the gaseous product stream 18 will be the same as the $H_2$/CO molar ratio in the synthesis gas 14 or feed synthesis gas 30, say 2.05. In such a case, controlling the $H_2$/CO molar ratio of the gaseous product stream 18 would not be effective to control the conversion achieved in the Fischer-Tropsch synthesis stage 16, since the $H_2$/CO molar ratio in the gaseous product stream 18 would always be the same as the $H_2$/CO molar ratio in the fresh synthesis gas 14 or feed synthesis gas 30, irrespective of the conversion. However, if the $H_2$/CO molar ratio of the fresh synthesis gas 14 or feed synthesis gas 30 to the Fischer-Tropsch synthesis stage 16 is lower than the consumption ratio, the $H_2$/CO molar ratio of the gaseous product stream 18 will be lower than the $H_2$/CO molar ratio in the fresh synthesis gas 14 or feed synthesis gas 30. For a given feed gas $H_2$/CO molar ratio, the drop in the tail gas $H_2$/CO molar ratio would be directly related to the extent of conversion achieved in the Fischer-Tropsch synthesis stage 16. Under such circumstances, the tail gas $H_2$/CO molar ratio can be used as a measure of the conversion and controlling the $H_2$/CO molar ratio of the gaseous product stream 18 (or e.g. the $H_2$/CO molar ratio of the cooled tail gas 26) would be effective to control the conversion achieved in the Fischer-Tropsch synthesis stage 16. Similarly, if the feed gas $H_2$/CO molar ratio to the Fischer-Tropsch synthesis stage 16 is higher than the consumption ratio, the $H_2$/CO molar ratio of the gaseous product stream 18 will be higher than the $H_2$/CO molar ratio of the fresh synthesis gas 14 or feed synthesis gas 30. For a given feed gas $H_2$/CO molar ratio, the rise in the tail gas $H_2$/CO molar ratio would be directly related to the extent of conversion achieved in the Fischer-Tropsch synthesis stage 16, and controlling the $H_2$/CO molar ratio of the gaseous product stream 18 would be effective to control the conversion achieved in the Fischer-Tropsch synthesis stage 16.

For a shifting catalyst with a reasonably constant $CO_2$ selectivity, the usage or consumption ratio will also be constant, but lower than about 2, e.g. for a shifting Fischer-Tropsch synthesis stage with a constant $CO_2$ selectivity of 20%, the overall usage ratio will be about 1.6. Similarly, if the feed $H_2$/CO ratio is at the usage ratio of about 1.6, the tail gas $H_2$/CO molar ratio would be the same as for the feed and controlling the $H_2$/CO molar ratio of the gaseous product stream 18 would not be effective to control the conversion achieved in the Fischer-Tropsch synthesis stage 16, since the $H_2$/CO molar ratio in the gaseous product stream 18 would always be the same as the $H_2$/CO molar ratio in the fresh synthesis gas 14 or feed synthesis gas 30, irrespective of the conversion. However, if the feed $H_2$/CO ratio is lower (or higher) than the usage ratio, the tail gas $H_2$/CO molar ratio will be lower (or higher) than that of the feed and controlling the $H_2$/CO molar ratio of the gaseous product stream 18 would be effective to control the conversion achieved in the Fischer-Tropsch synthesis stage 16.

Example 1

Figure 2:
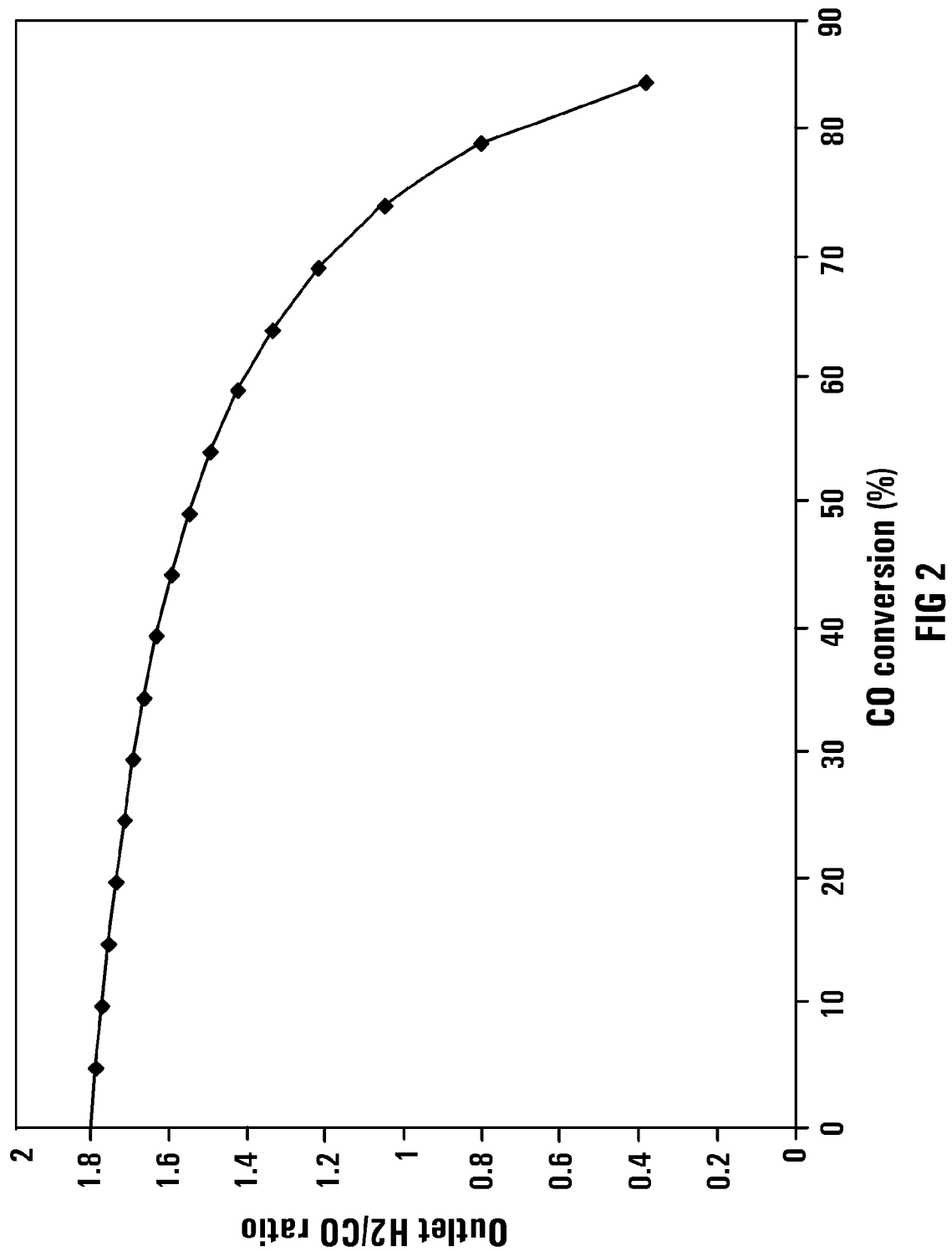

A non-shifting Fischer-Tropsch catalyst with an $H_2$ and CO consumption ratio of 2.05 is operated with a fresh synthesis gas feed having an $H_2$/CO molar ratio of 1.8. For any assumed overall CO conversion, the tail gas $H_2$/CO molar ratio can be calculated, as depicted in FIG. 2. This unique relationship between the overall CO conversion and the tail gas $H_2$/CO molar ratio is independent of whether or not an internal recycle is applied around the reactor. Therefore, the tail gas $H_2/CO$ molar ratio can be used as a fair estimate for the overall conversion as suggested in accordance with the invention.

Figure 3:
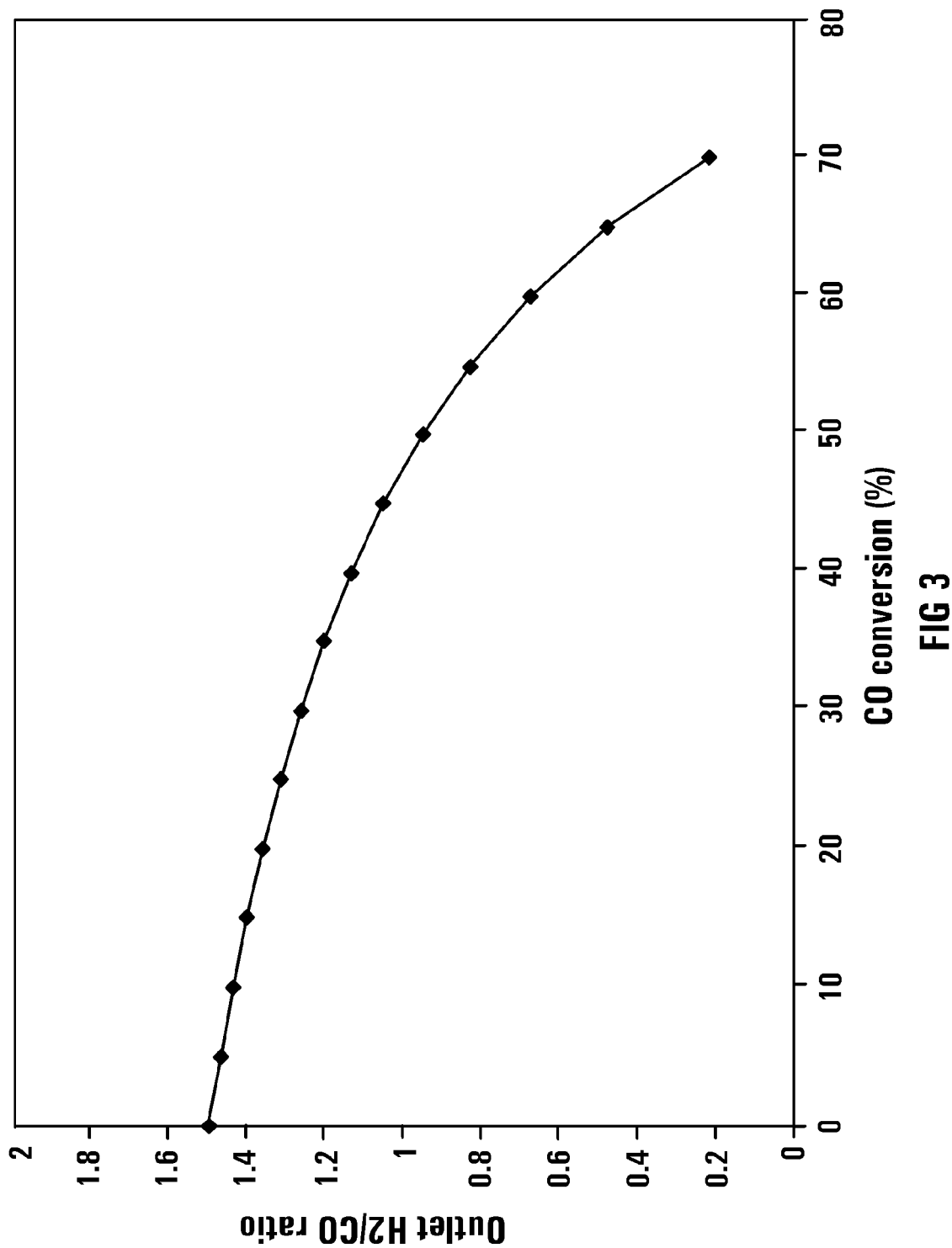

Similarly, the tail gas $H_2/CO$ molar ratio has been calculated as a function of the overall CO conversion for the case of a non-shifting Fischer-Tropsch catalyst with an $H_2$ and CO consumption ratio of 2.05, operated with a fresh synthesis gas feed having an $H_2/CO$ molar ratio of 1.5 (see FIG. 3). Clearly the relationship shown in FIG. 3 is different from that shown in FIG. 2. Nevertheless, for this latter case where the feed gas $H_2/CO$ molar ratio is maintained constant at a value of 1.5, the process of the invention can be used effectively to control the conversion achieved in the Fischer-Tropsch reactor.

Example 2

Figure 4:
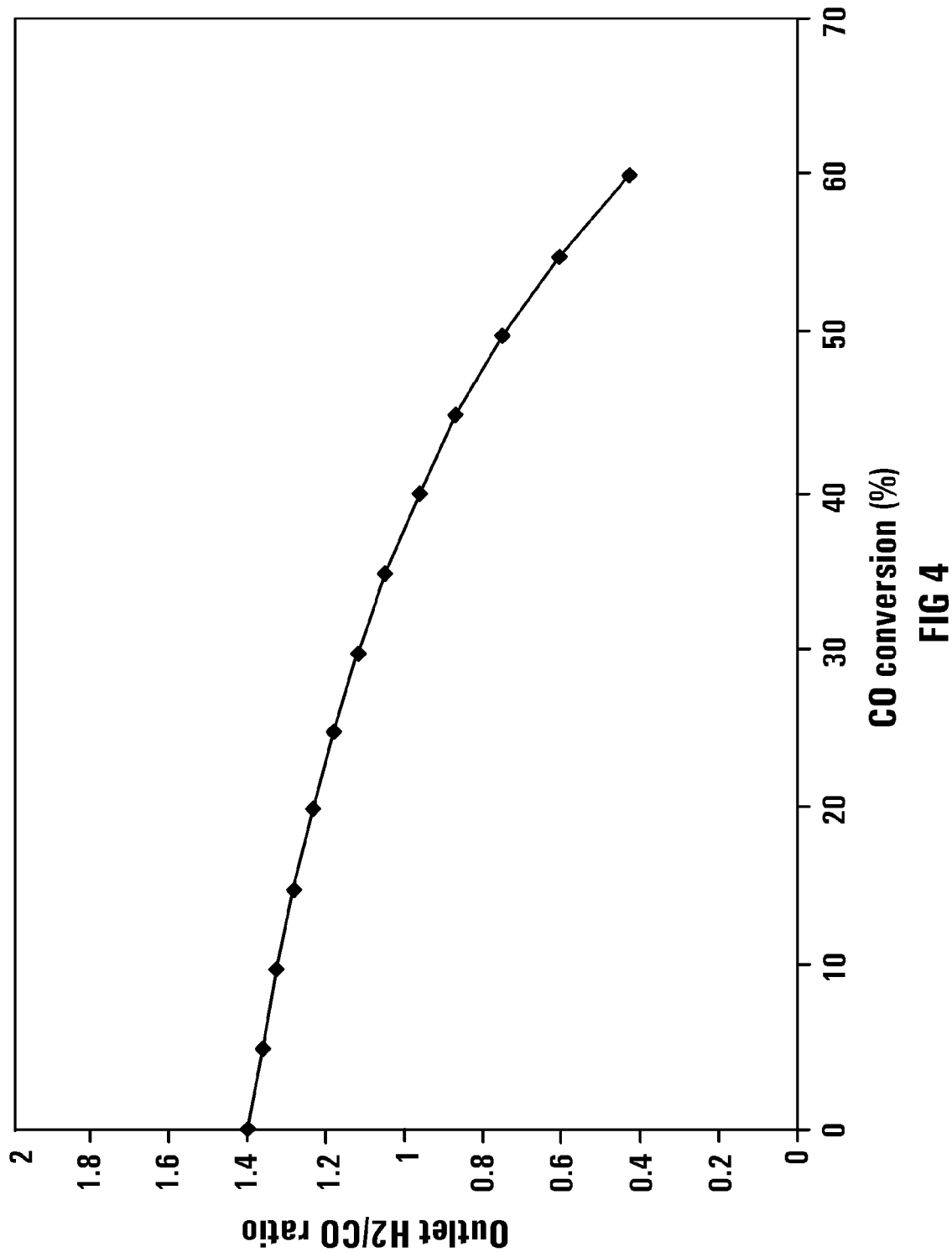

A non-shifting Fischer-Tropsch process is operated under recycle. The $H_2/CO$ molar ratio of a total feed stream, i.e. a combined feed stream comprising fresh synthesis gas and an internal recycle, is controlled at a target value of 1.4. The tail gas $H_2/CO$ molar ratio is depicted in FIG. 4 as a function of the per pass CO conversion, which also indicates a unique relationship. Therefore, the tail gas $H_2/CO$ molar ratio can be used fairly to estimate the per pass conversion achieved in a Fischer-Tropsch reactor.

Example 3

Figure 5:
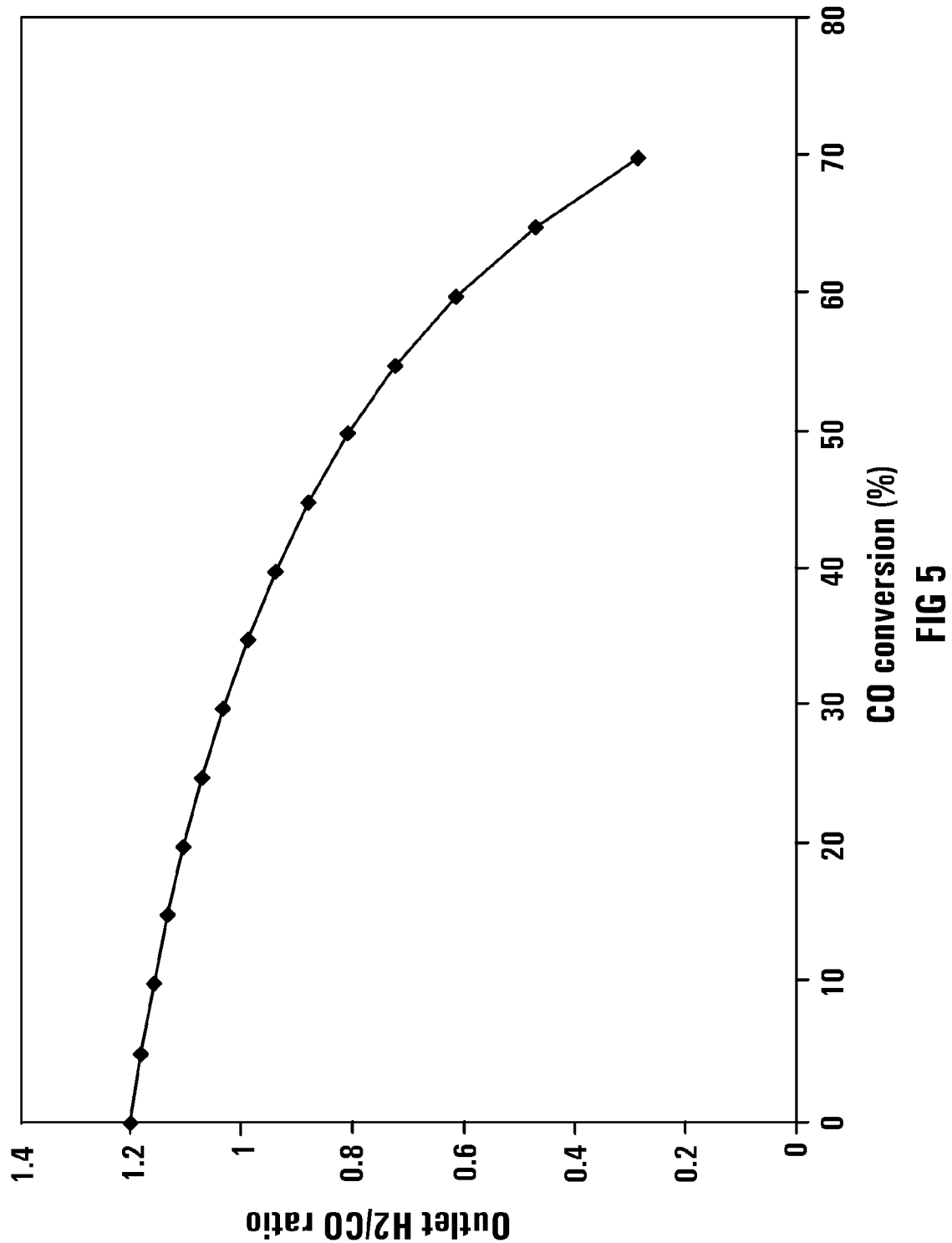
Figure 6:
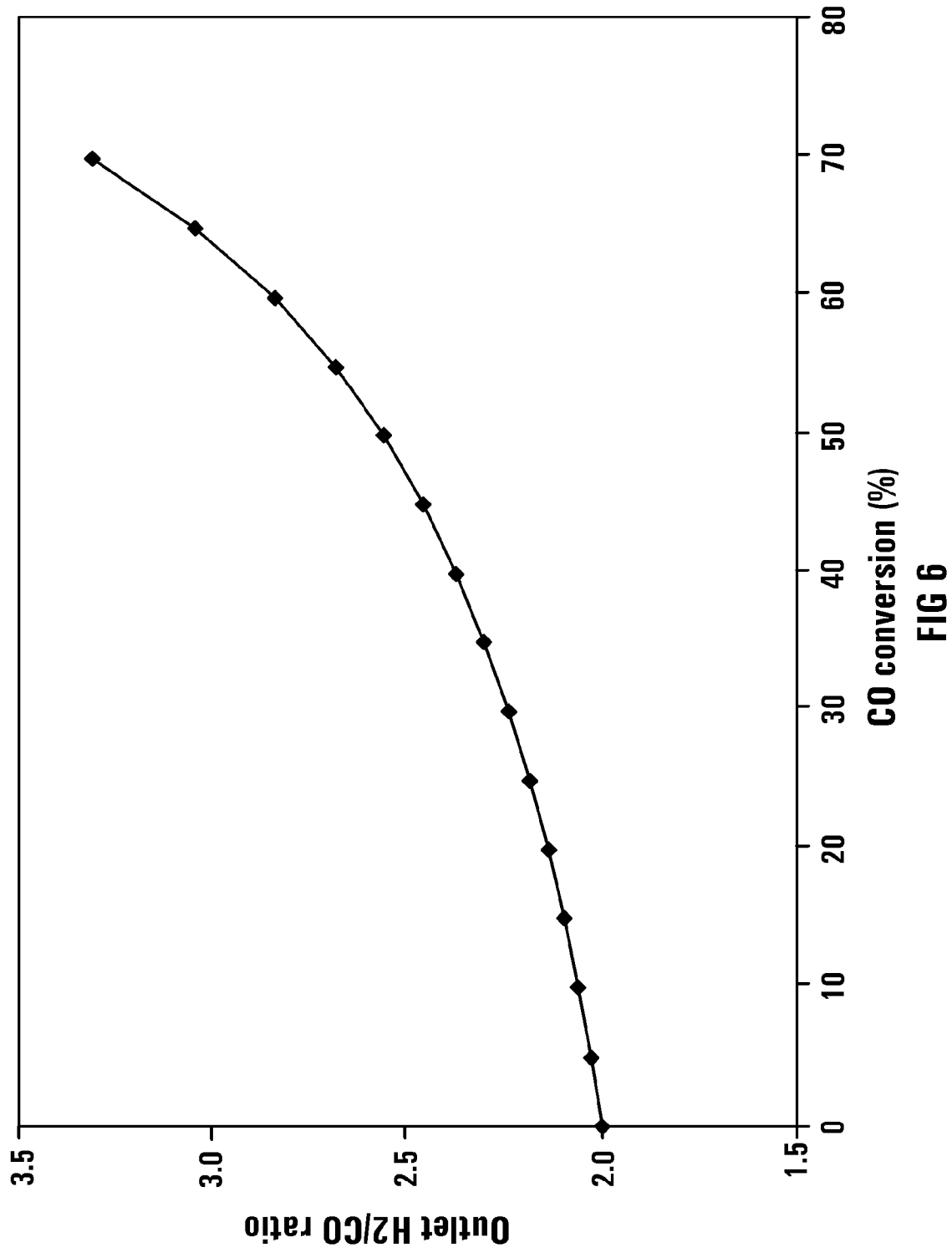

A shifting Fischer-Tropsch process with a $CO_2$ selectivity of 15% is operated with a feed $H_2/CO$ molar ratio of 1.2. The tail gas $H_2/CO$ molar ratio is presented as a function of the CO conversion in FIG. 5, showing the unique declining relationship between tail gas $H_2/CO$ ratio and increasing conversion. On the other hand, as shown in FIG. 6, a shifting Fischer-Tropsch process with a $CO_2$ selectivity of 20% operated with a feed $H_2/CO$ molar ratio of 2 yields a unique, but increasing tail gas $H_2/CO$ molar ratio with increasing conversion. In both these cases, the tail gas $H_2/CO$ molar ratio can be used fairly to estimate the per pass conversion achieved in a Fischer-Tropsch reactor.

The invention claimed is:

1. A process to produce Fischer-Tropsch products, the process comprising
    feeding feed synthesis gas, with a feed synthesis gas $H_2/CO$ ratio that is within 10% of a target $H_2/CO$ ratio for the feed synthesis gas, to a Fischer-Tropsch synthesis stage;
    converting a portion of said feed synthesis gas to Fischer-Tropsch products in the Fischer-Tropsch synthesis stage;
    withdrawing said Fischer-Tropsch products from the Fischer-Tropsch synthesis stage;
    obtaining a Fischer-Tropsch synthesis stage tail gas which comprises unconverted $H_2$ and CO; and
    manipulating operating conditions of the Fischer-Tropsch synthesis stage to achieve a tail gas $H_2/CO$ ratio that is within 10% of a target $H_2/CO$ ratio for the tail gas, said target tail gas $H_2/CO$ ratio differing by at least 10% from the target feed synthesis gas $H_2/CO$ ratio and said target $H_2/CO$ ratio for the feed synthesis gas and said target $H_2/CO$ ratio for the tail gas being selected to provide a desired per pass conversion of CO reactant in the Fischer-Tropsch synthesis stage.

2. The process as claimed in claim 1, in which the Fischer-Tropsch synthesis stage is a non-shifting Fischer-Tropsch synthesis stage employing a cobalt-based catalyst.

3. The process as claimed in claim 1, which comprises recycling a portion of the Fischer-Tropsch synthesis stage tail gas which comprises unconverted $H_2$ and CO to the Fischer-Tropsch synthesis stage and in which the feed synthesis gas is thus a combination of fresh synthesis gas and recycled Fischer-Tropsch synthesis stage tail gas, whether combined into a single stream or fed separately to the Fischer-Tropsch reaction stage.

4. The process as claimed in claim 3, in which the ratio of the recycled Fischer-Tropsch synthesis stage tail gas to the fresh synthesis gas is manipulated to achieve said feed synthesis gas with a feed synthesis gas $H_2/CO$ ratio that is within 10% of a target $H_2/CO$ ratio for the feed synthesis gas.

5. The process as claimed in claim 3, which comprises operating a synthesis gas generation stage to produce said fresh synthesis gas, the synthesis gas generation stage being operated to produce fresh synthesis gas with a constant target fresh synthesis gas $H_2/CO$ ratio.

6. The process as claimed in claim 5, in which the fresh synthesis gas is maintained at a constant flow rate and in which the operating conditions or parameters of the Fischer-Tropsch synthesis stage are adjusted in order to achieve the target tail gas $H_2/CO$ ratio.

7. The process as claimed in claim 5, which comprises recycling at least a portion of the Fischer-Tropsch synthesis stage tail gas, or a CO and/or $H_2$ containing gas stream derived from the Fischer-Tropsch synthesis stage tail gas, to the synthesis gas generation stage, and manipulating the rate at which the Fischer-Tropsch synthesis stage tail gas or said gas stream derived from the Fischer-Tropsch synthesis stage tail gas is recycled to the synthesis gas generation stage to produce said fresh synthesis gas with a constant target fresh synthesis gas $H_2/CO$ ratio.

8. The process as claimed in claim 3, which comprises operating a synthesis gas generation stage to produce said fresh synthesis gas, the synthesis gas generation stage being operated to produce fresh synthesis gas with a constant target fresh synthesis gas $H_2/CO$ ratio, the process further comprising feeding the recycled Fischer-Tropsch synthesis stage tail gas to the Fischer-Tropsch synthesis stage in a fixed ratio to the fresh synthesis gas, thereby achieving said constant target feed synthesis gas $H_2/CO$ ratio.

* * * * *